US00PP26569P3

(12) United States Plant Patent
Olesen

(10) Patent No.: US PP26,569 P3
(45) Date of Patent: Apr. 5, 2016

(54) GARDEN ROSE PLANT NAMED 'POULREN014'

(50) Latin Name: ***Rosa* hybrid**
Varietal Denomination: Poulren014

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 268 days.

(21) Appl. No.: 13/986,925

(22) Filed: Jun. 14, 2013

(65) Prior Publication Data

US 2014/0373224 P1 Dec. 18, 2014

(51) Int. Cl.
*A01H 5/00* (2006.01)
*A01H 5/02* (2006.01)

(52) U.S. Cl.
USPC ..... Plt./108
CPC ..... *A01H 5/0222* (2013.01)

(58) Field of Classification Search
USPC ..... Plt./108
See application file for complete search history.

(56) References Cited

PUBLICATIONS

The International Contest of New Roses. Jun. 2011. pp. 1-3.*

* cited by examiner

*Primary Examiner* — Annette Para

(57) ABSTRACT

A new garden rose plant of the grandiflora class which has abundant, red-purple flowers and attractive foliage. This new and distinct variety has shown to be uniform and stable in the resulting generations from asexual propagation.

2 Drawing Sheets

Botanical designation: *Rosa* hybrid.
Variety denomination: 'Poulren014'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2000 and the resulting seeds were planted in a controlled environment in Fredensborg, Denmark. The new variety, named 'Poulren014', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant red-purple, fragrant flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulren014' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulren014' was selected in the spring of 2001 by the inventor as a single plant from the progeny of the aforementioned hybridization.

Asexual reproduction of 'Poulren014' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulren014' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren014'.

Specifically illustrated in FIG. 1 are open flowers, flower parts, stems, and leaves.

DETAILED DESCRIPTION OF THE VARIETY

Figure 1:
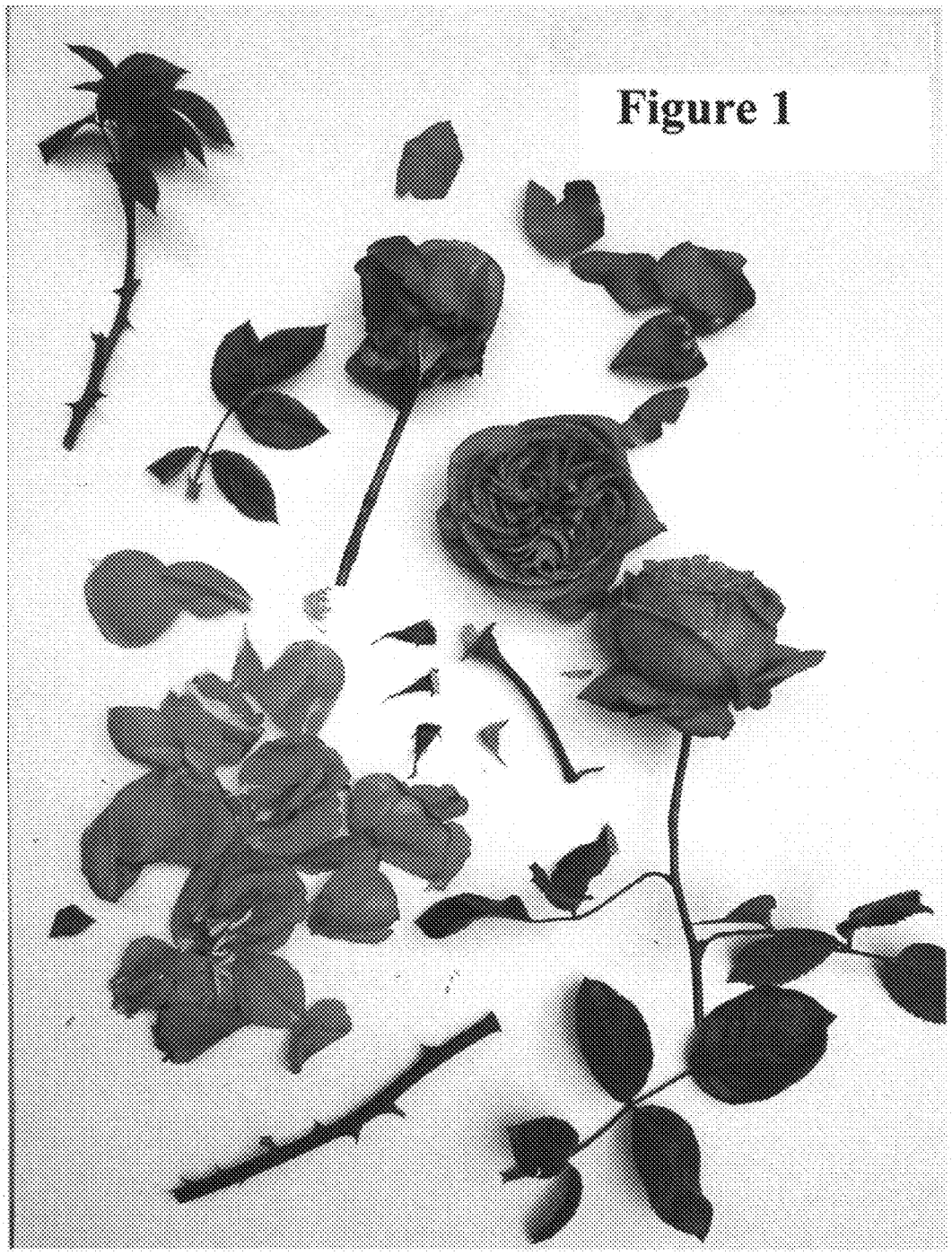
Figure 2:
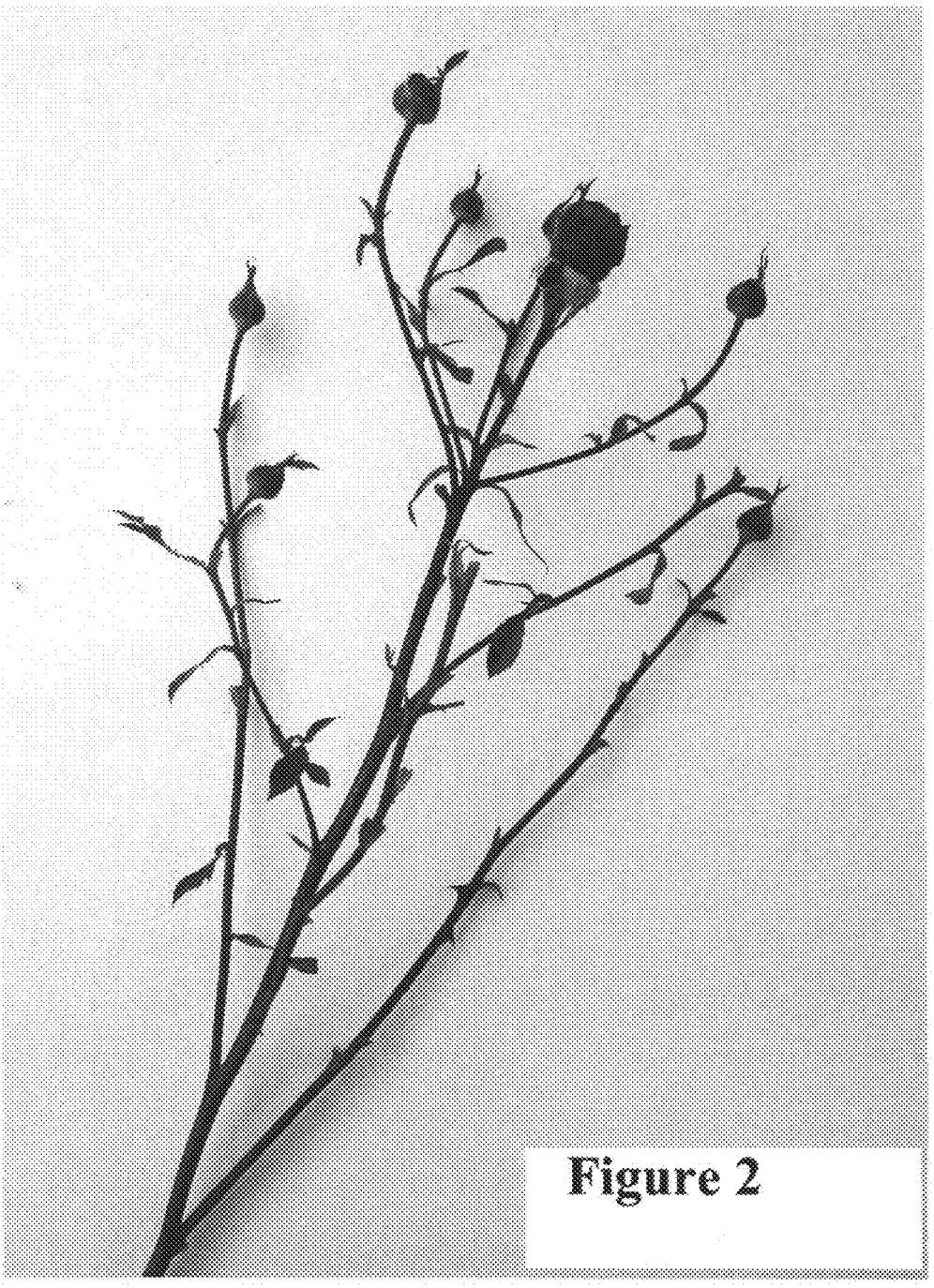
FIG. 2 shows stems, peduncles, and other flower parts.

The following is a description of 'Poulren014', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Ausbord', U.S. Plant Pat. No. 7,220 are compared to 'Poulren014' in Chart 1.

CHART 1

| | 'Poulren014' | 'Ausbord' |
|---|---|---|
| Color & Fragrance | Strong Pink, Very Fragrant | Strong Pink, Very Fragrant |
| Flower Diameter | 9 cm | 11 cm |
| Plant height | 100 cm | 120-150 cm |

Flower and Flower Bud

Blooming habit: Continuous.

Flower bud:

*Size*.—Upon opening, 22 mm in length from base of receptacle to end of bud. Bud diameter is 20 mm.

*Bud form*.—Globose.

*Bud color*.—As sepals divide petals are Red-Purple Group 59A.

*Sepal inner surface*.—Color: Green Group 138A, and Greyed-Red Group 182A at the sepal base. Surface: Smooth and moderately pubescent.

*Sepal outer surface*.—Color: Yellow-Green Group 144A with very strong anthocyanin the color of Greyed-Purple Group 187A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—30 mm long by 10 mm wide.

*Receptacle*.—Texture: Smooth. Size: 8 mm in height by 13 mm wide. Color: Yellow-Green Group 144A. Anthocyanic pigments the color of Greyed-Purple Group 187A. Shape: Funnel shaped.

*Pedicel*.—Surface: Smooth, with a few small prickles. Length: 60 to 70 mm. Diameter: 4 mm on average. Color: Greyed-Purple Group 187A. Strength: Strong.

*Peduncle*.—Length: 5 to 30 cm. Diameter: 3 to 4 mm. Color: Yellow-Green Group 145A with strong intonations of Greyed-Purple Group 187A to Greyed-Purple Group 183A. Texture: Smooth.

Flower bud development: Flower buds are borne in clusters of 5 to 9 flower buds per stem, resembling a corymb.

Flower bloom:

*Fragrance*.—Heavy citrus perfume.

*Duration*.—The blooms have a duration on the plant of approximately 14 days. Petals fall cleanly away from plant after flowers have fully matured.

*Size*.—Flower diameter is 90 mm when open. Flower depth is 50 mm.

*Flower shape*.—General shape is a quartered-rosette, very double, with many overlapping petals packed into quarter sections.

*Shape of flower, side view*.—The upper portion is flat. Lower portion is a flattened convex.

Petalage: Under normal conditions, flowers have 90 petals total, 15 of which are petaloids.

General tonality of flower: Open flowers are Red-Purple Group 67A with intonations of Red-Purple Group 71C.

Petal color:

*Upon opening, outer and inner petals*.—Upper surface: Red-Purple Group 71C. Lower surface: Red-Purple Group 71B with light shades of Red-Purple Group 72B.

*Basal petal spots, upon opening*.—Upper surface: Yellow Group 3C. Lower surface: Yellow Group 3C.

*After opening, outer and inner petals*.—Upper surface: Red-Purple Group N57B and Red-Purple Group 71C blend. Lower surface: Red-Purple Group N57B and Red-Purple Group 71B blend.

*Basal petal spots, after opening*.—Upper surface: Yellow Group 3C. Lower surface: Yellow Group 3C.

Petals:

*Petal reflex*.—Somewhat reflexed.

*Margin*.—Entire and uniform. Weak strong undulations of margin observed.

*Shape*.—Narrow elliptic. Apex shape: Rounded. Base shape: Acute.

*Size*.—50 mm (l)×48 mm (w).

*Texture*.—Smooth.

*Thickness*.—Average.

Petaloids:

*Size*.—20 mm (l) by 13 mm (w).

*Quantity*.—15 on average.

*Shape*.—Apex is rounded, base is acute.

*Color*.—Upper Red-Purple Group 71C, splashed with Red Group 55B. Lower Red-Purple Group 71B with light shades of Red-Purple Group 72B. Petaloid spots on the upper and lower side are Yellow Group 3C.

Reproductive organs:

*Pollen*.—None observed.

*Anthers*.—Size: 5 mm in length. Color: Yellow Group 10B. Quantity: 50 on average.

*Filaments*.—Color: Yellow Group 4B. Length: 10 mm.

*Pistils*.—Length: 8 mm. Quantity: 35 on average.

*Stigmas*.—Color: Greyed-Yellow Group 160 C.

*Styles*.—Color: Red Group 39A.

*Location of stigmas*.—Level in location relative to the length of the filaments and the height of the anthers.

*Hips*.—None Observed.

Plant

Plant growth: Upright, bushy. Plants are 100 cm in height, and 100 cm wide.

Stems:

*Color*.—Juvenile growth: Greyed-Purple Group 187A. Mature growth: Yellow-Green Group 146B with intonations of Greyed-Purple Group 183A.

*Length*.—On average, canes are 5 cm from the base of the plant to the flowering portion.

*Diameter*.—6 to 7 mm.

*Internodes*.—On mature canes, there is an average distance of 70 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 10 mm.

*Shape*.—Upper portion is linear. Lower portion is deep concave.

*Color*.—Juvenile prickles: Greyed-Red Group 182A. Mature prickles: Greyed-Red Group 182A.

Plant foliage:

*Compound leaf*.—170 mm (l)×120 (w).

*Quantity*.—2 leaves per 10 cm of stem on average.

*Leaf bearing angle to the stem*.—90 degrees.

*Color of juvenile foliage*.—Upper side: Greyed-Purple Group 187A. Lower side: Greyed-Purple Group 187B.

*Color of mature foliage*.—Upper side: Yellow-Green Group 147A. Lower side: Yellow-Green Group 147B.

Plant leaves and leaflets:

*Stipules*.—Size: 15 mm in length. Quantity: 2 per compound leaf. Shape: Linear, slightly broad based with outward extending apecies. Margins: Finely serrated. Color: Yellow-Green Group 144A.

*Petiole*.—Length: 40 mm. Diameter: 2 mm. Upper surface: Color: Greyed-Red Group 178A. Lower surface: Color: Yellow-Green Group 144B. Observations: Small prickles.

*Rachis*.—Length: 65 mm. Upper surface: Greyed-Red Group 178A. Lower surface: Yellow-Green Group 144B. Observations: Small prickles.

*Leaflet*.—Quantity: Normal number of leaflets leaves in middle of the stem is 5 leaflets. Margins: Serrated. Size: Average size of the terminal leaflet on normal leaves is 65 mm in length by 50 mm wide. Shape: Generally orbicular. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the grandiflora rose class named 'Poulren014', substantially as illustrated and described herein, due to its abundant red-purple flowers, disease resistance, and extended period of bloom.

* * * * *